United States Patent
Guidry et al.

(10) Patent No.: US 10,357,394 B2
(45) Date of Patent: Jul. 23, 2019

(54) OSTOMY POUCH REPLACEMENT DEVICE

(71) Applicants: Liney Guidry, Baton Rouge, LA (US); Theresa Johnson, Simpsonville, SC (US); Reed Johnson, Cumming, GA (US); Bruce Johnson, Simpsonville, SC (US)

(72) Inventors: Liney Guidry, Baton Rouge, LA (US); Theresa Johnson, Simpsonville, SC (US); Reed Johnson, Cumming, GA (US); Bruce Johnson, Simpsonville, SC (US)

(*) Notice: Subject to any disclaimer, the term of this patent is extended or adjusted under 35 U.S.C. 154(b) by 0 days.

(21) Appl. No.: 15/725,523

(22) Filed: Oct. 5, 2017

(65) Prior Publication Data

US 2018/0028347 A1    Feb. 1, 2018

Related U.S. Application Data

(63) Continuation-in-part of application No. 14/960,759, filed on Dec. 7, 2015, now Pat. No. 10,130,505.

(51) Int. Cl.
  *A61F 5/44* (2006.01)
  *A61F 5/448* (2006.01)
  *A61F 5/443* (2006.01)

(52) U.S. Cl.
  CPC ........... *A61F 5/4404* (2013.01); *A61F 5/443* (2013.01); *A61F 5/448* (2013.01); *A61F 5/4401* (2013.01); *A61F 2005/4402* (2013.01)

(58) Field of Classification Search
  CPC combination set(s) only.
  See application file for complete search history.

(56) References Cited

U.S. PATENT DOCUMENTS

| | | | | |
|---|---|---|---|---|
| 3,520,301 A | * | 7/1970 | Fenton | A61F 5/448 604/338 |
| 4,187,850 A | * | 2/1980 | Gust | A61F 5/445 604/338 |
| 4,344,433 A | * | 8/1982 | Smith | A61F 5/445 604/344 |
| 4,344,435 A | | 8/1982 | Aubin | |

(Continued)

FOREIGN PATENT DOCUMENTS

CN    204106295 U1    1/2015

*Primary Examiner* — Tatyana Zalukaeva
*Assistant Examiner* — Guy K Townsend
(74) *Attorney, Agent, or Firm* — Southeast IP Group, LLC.; Thomas L. Moses

(57) ABSTRACT

An ostomy pouch replacement device allows ostomates with a surgically created stoma to collect, contain and dispose of bodily fluids during hygienic maintenance. The device is customizable to each ostomate's unique stoma diameter and provides a disposable waste receptacle having a hollow absorbent section and a solid absorbent section for sanitary, discreet and odorless disposal of both urine and excrement. The disposable waste receptacle may include a super absorbent polymer powder that becomes a gel in the presence of liquid. The device preferably consists of a disposable waste receptacle that may be positioned over the stoma and includes an absorbent inner material for capturing waste, a cap or plug for sealing the device after use, and a collar stand for pressing an adhesive wafer to the skin and for holding the assembled device in an upright position.

13 Claims, 7 Drawing Sheets

(56) References Cited

U.S. PATENT DOCUMENTS

| | | | | |
|---|---|---|---|---|
| 4,686,355 A * | 8/1987 | Lay | ............ | A61F 5/445 |
| | | | | 108/33 |
| 4,726,354 A * | 2/1988 | Fujita | ............ | A61F 5/445 |
| | | | | 600/32 |
| 4,850,986 A * | 7/1989 | Temple | ............ | A61F 5/44 |
| | | | | 604/355 |
| 5,125,916 A | 6/1992 | Panebianco et al. | | |
| 5,312,384 A * | 5/1994 | Temple | ............ | A61F 5/44 |
| | | | | 604/355 |
| 5,421,827 A * | 6/1995 | Temple | ............ | A61F 5/451 |
| | | | | 383/67 |
| 6,186,990 B1 * | 2/2001 | Chen | ............ | A61F 5/44 |
| | | | | 4/451 |
| 6,409,709 B1 * | 6/2002 | Recto | ............ | A61F 5/445 |
| | | | | 604/327 |
| 6,579,271 B1 * | 6/2003 | Aruffo | ............ | A61F 17/00 |
| | | | | 206/440 |
| 6,916,312 B2 * | 7/2005 | Kondo | ............ | A61F 5/443 |
| | | | | 604/277 |
| 6,929,627 B2 * | 8/2005 | Mahoney | ............ | A61F 5/445 |
| | | | | 604/332 |
| 7,083,569 B2 * | 8/2006 | Boulanger | ............ | A61F 5/445 |
| | | | | 600/32 |
| 2003/0040727 A1 * | 2/2003 | Boulanger | ............ | A61F 5/445 |
| | | | | 604/332 |
| 2012/0123379 A1 | 5/2012 | Forsell | | |
| 2012/0277700 A1 * | 11/2012 | Amer, Jr. | ............ | A61F 5/445 |
| | | | | 604/332 |
| 2017/0156917 A1 * | 6/2017 | Guidry | ............ | A61F 5/4404 |
| 2018/0028347 A1 * | 2/2018 | Guidry | ............ | A61F 5/4404 |

\* cited by examiner

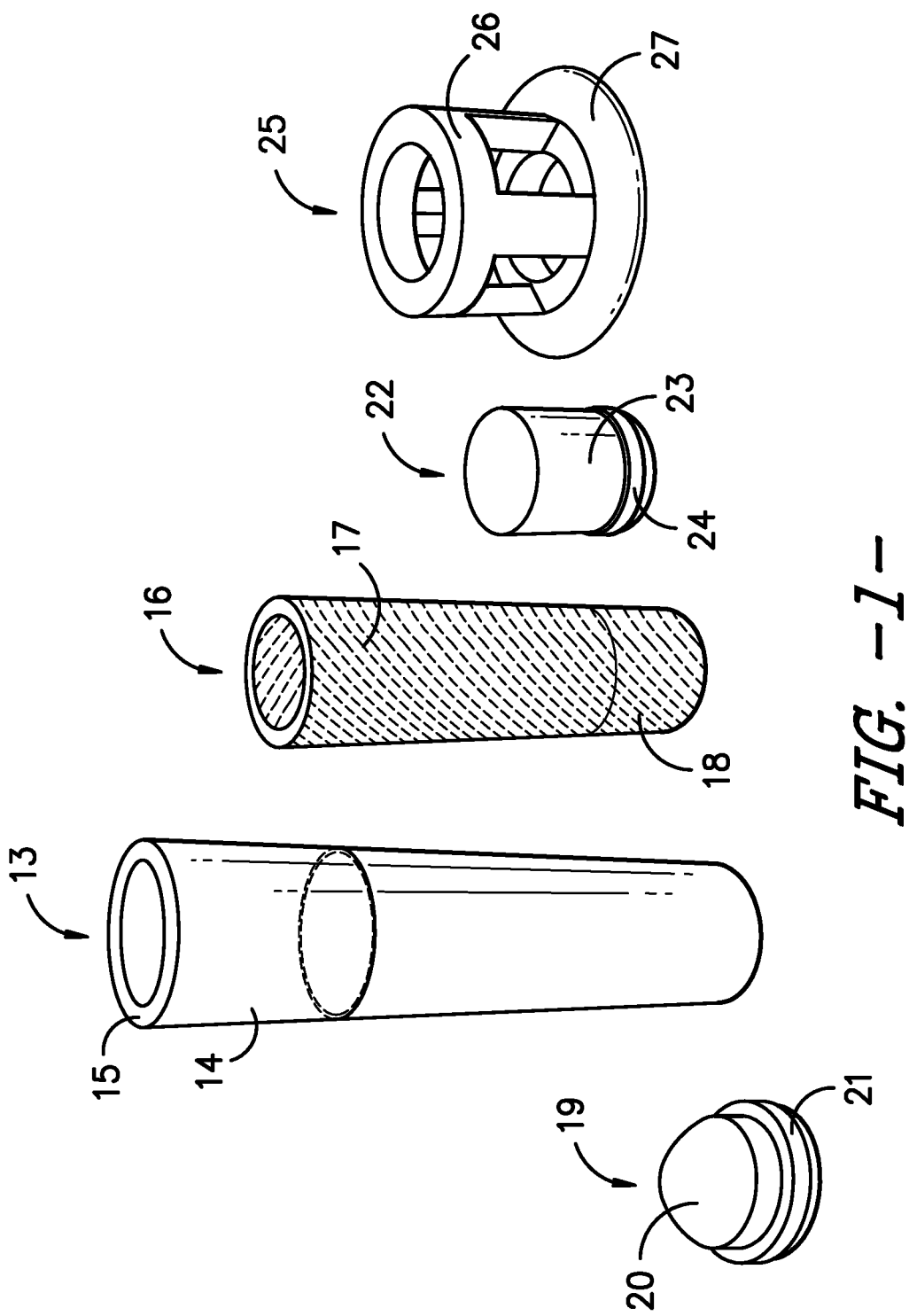
FIG. -1-

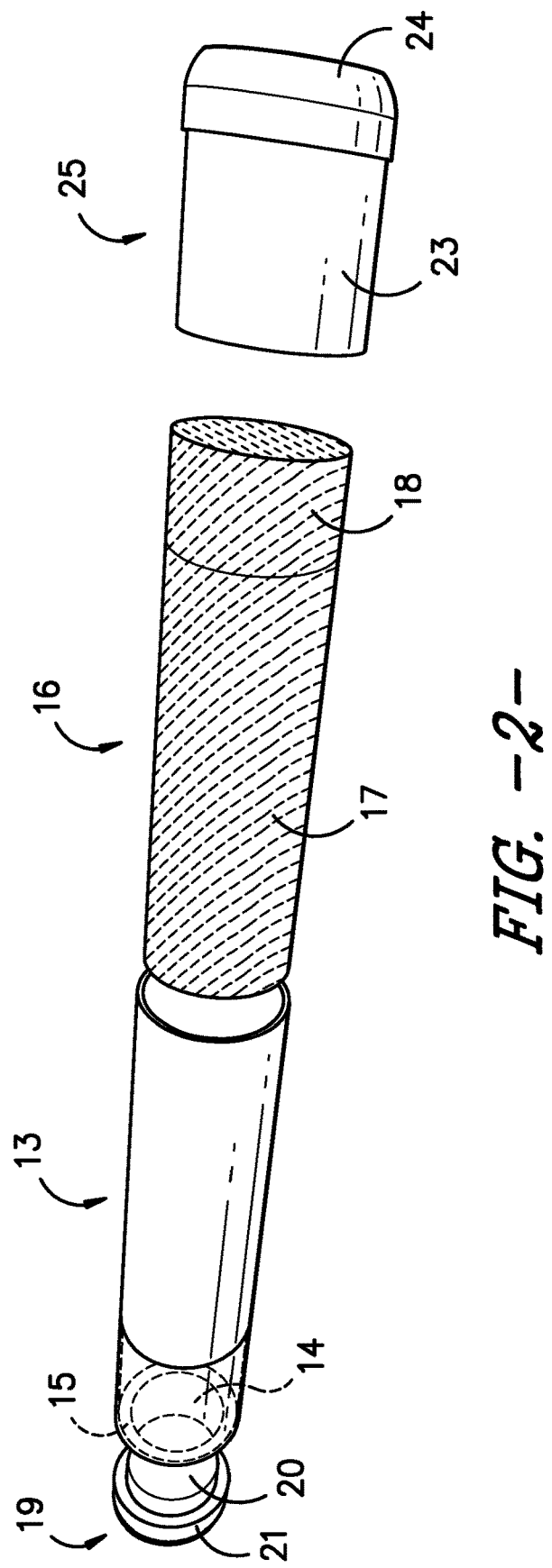
FIG. -2-

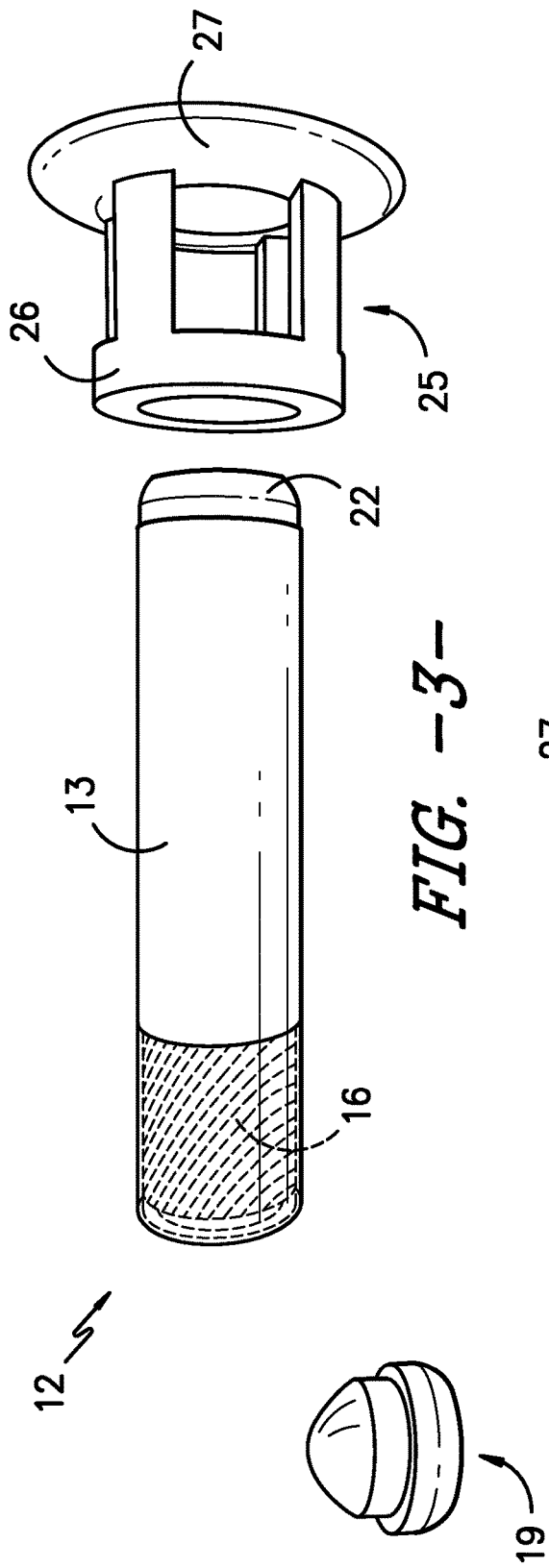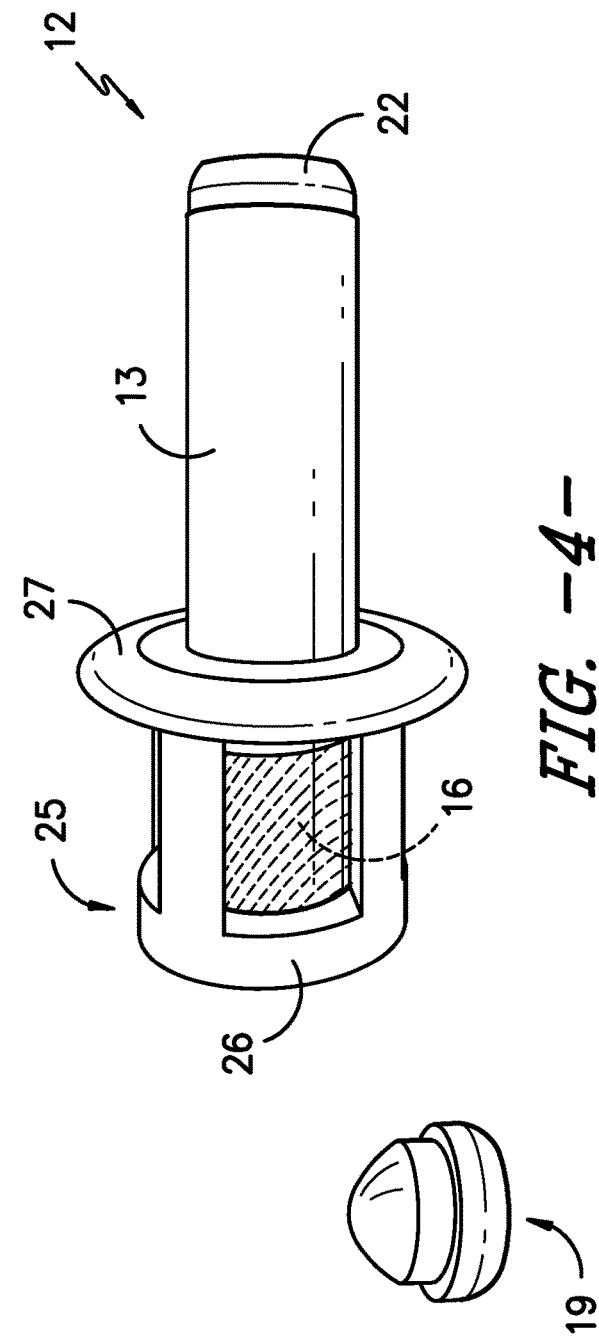

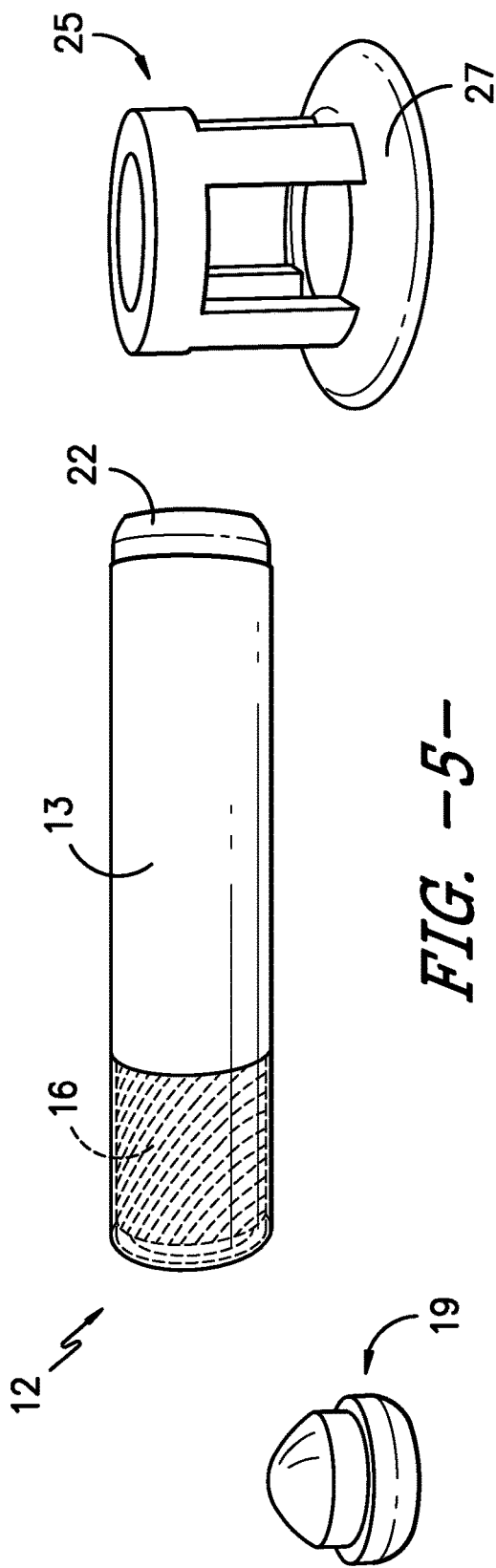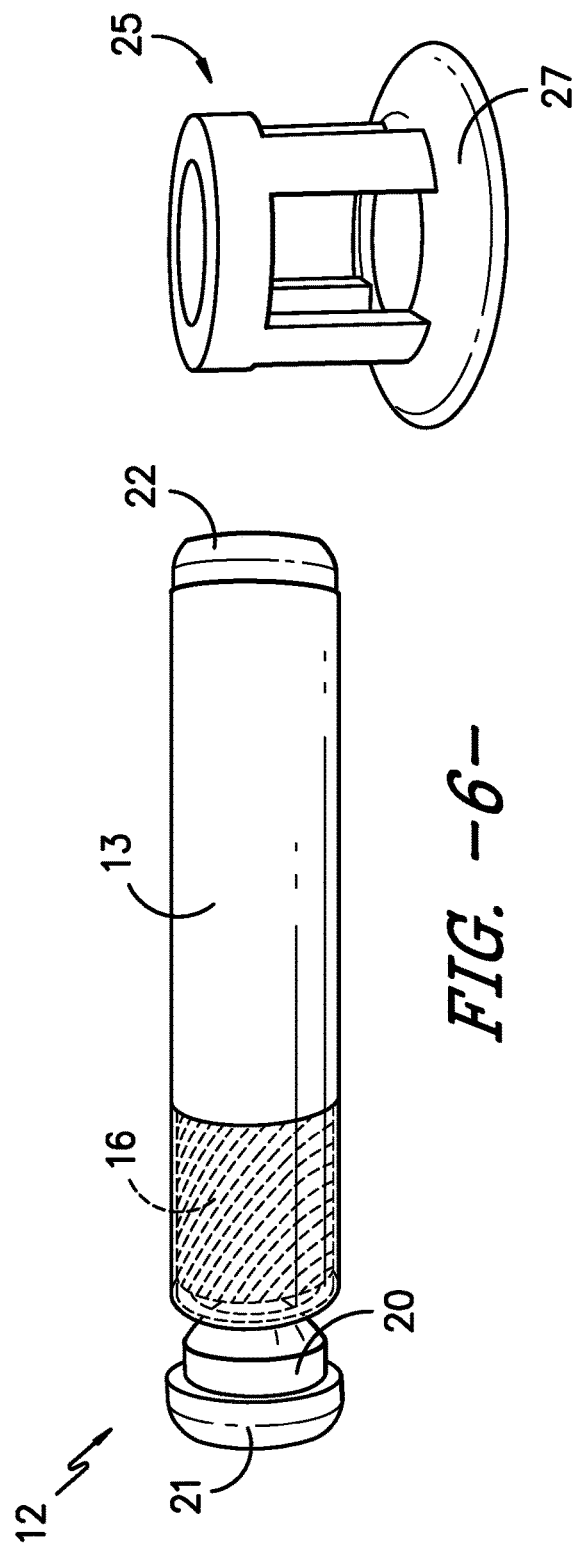
FIG. -5-
FIG. -6-

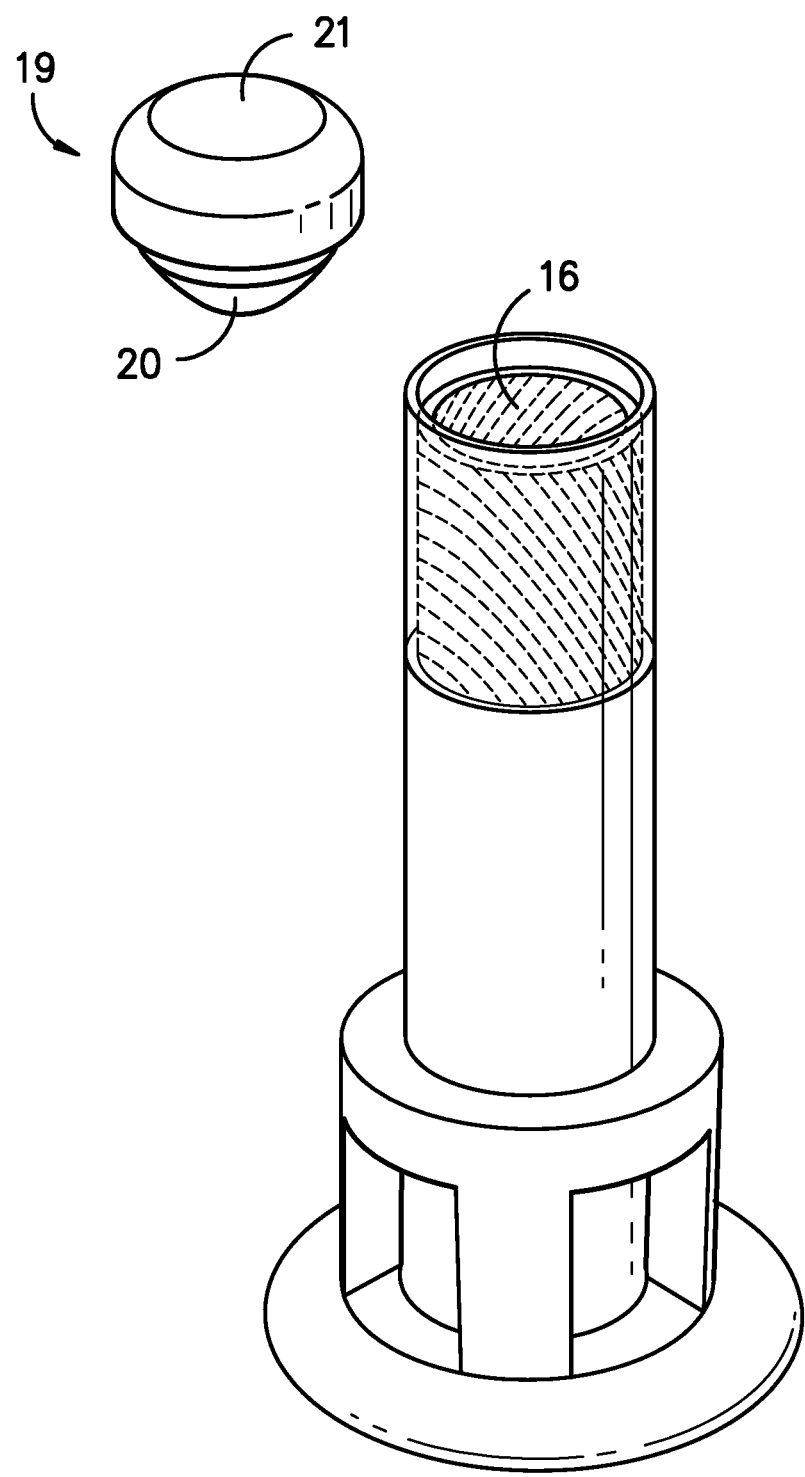
FIG. -7-

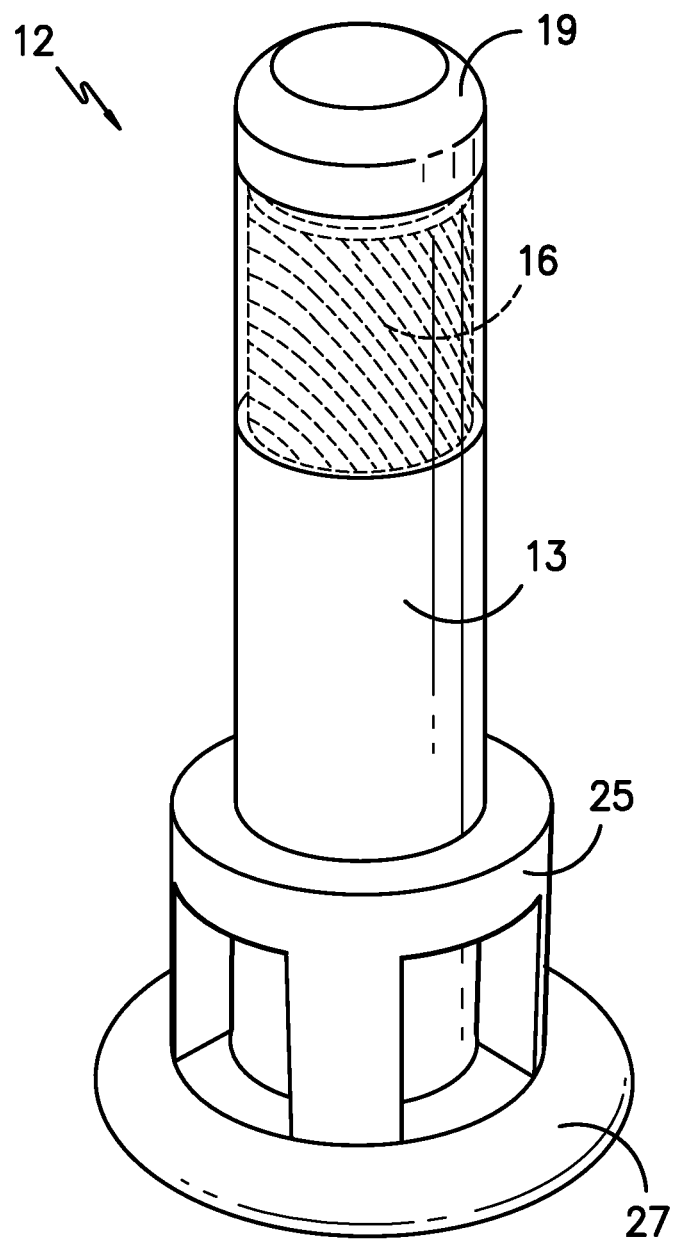
FIG. -8-

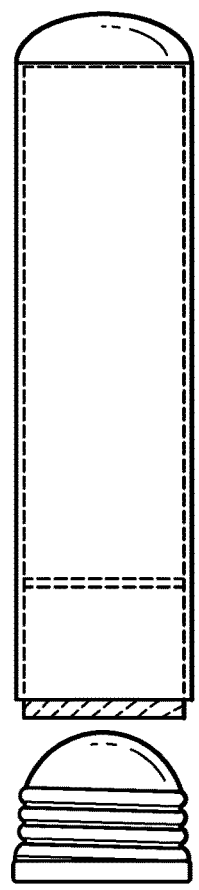
FIG. -9-
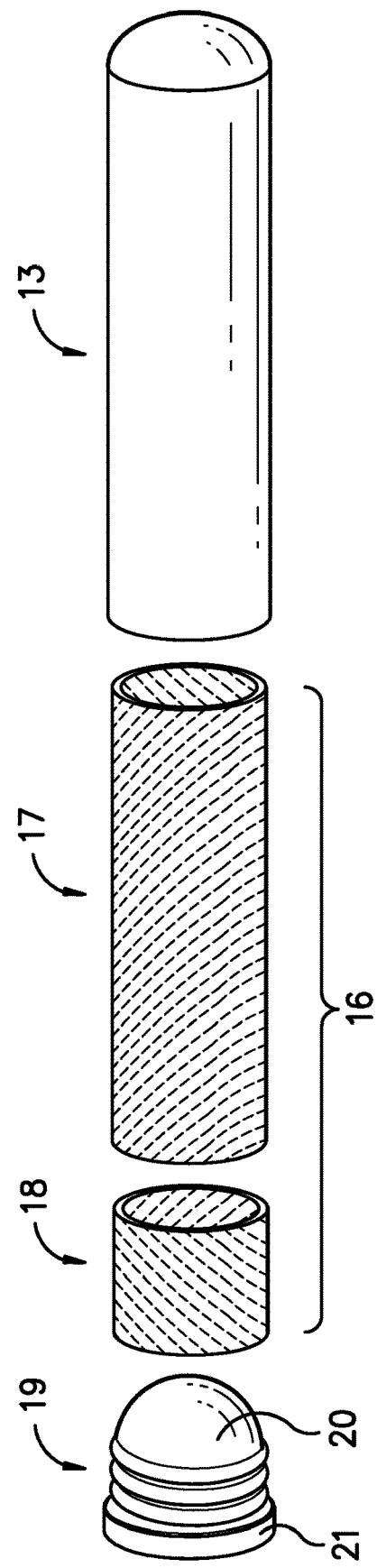
FIG. -10-

OSTOMY POUCH REPLACEMENT DEVICE

BACKGROUND OF THE INVENTION

The present invention relates to a personal care apparatus and, in particular, to an apparatus for collecting, containing and disposing of waste matter, during the replacement of a stoma bag for those people having had surgical operations for removing a bladder or colon.

Surgical procedures such as colostomies, cystostomies, urostomies and ileostomies involve rerouting of the colon or ureter so that waste materials can be discharged through an artificial opening formed in the ostomy patient's (also referred to herein as ostomate) body. This artificial opening, called a stoma, is typically located in the abdomen and may be about 0.5 to 1.0 inch or more in diameter. A stoma is connected directly to the kidney by a rerouted ureter or to the intestines by the rerouted colon and the discharge of waste matter in each instance is made through the stoma.

The new artificial opening, or stoma, made on the abdominal wall, has no voluntary sphincter control by the ostomate. Collection of involuntary waste seepage is by bag or other receptacle attached to the ostomate's body. Disposable and semi-disposable bags for such purposes are available from several commercial sources. The disposable bags come as assembled units which are applied to the body. Such bags are attached to the body over the stoma by means of a ring-like member known as a wafer or face plate and a sealing ring of double sided adhesive which must be assembled and positioned over the stoma with precision to achieve a reliable attachment and seal. It is essential that this ring be mounted directly and concentrically over the stoma and further, that it be tightly secured to the body, otherwise, leakage of waste onto the surrounding skin area can occur. After removal of the filled bag, the common practice in the past has been to first clean and dry the stoma and surrounding skin area before application of the sealing ring to the skin, followed by connection of the face plate to the sealing ring and then attachment of a new bag to the face plate. It is most important that the skin area surrounding the stoma be kept clean and dry during replacement of the bag to avoid infection and to achieve a good connection between the skin, sealing ring and face plate. Adhesive tape is sometimes applied over the edges of the face plate and sealing ring for extra reinforcement. Inadvertent disconnection of a bag can cause considerable inconvenience and embarrassment to an ostomate.

In the replacement of the ostomy appliance, the general procedure is first to remove the ring and the receptacle. The ostomate applies an absorbent material of choice on top of the stoma to absorb any waste matter and prevent it from leaking onto the surrounding skin prior to the application of the adhesive. The surrounding skin must be cleaned and dried. This is generally accomplished by the use of a commercially available "prep" agent, which removes the skin oils, cleans the skin, and leaves a dry skin surface. Upon application of the adhesive, the absorbent material is removed from the stoma and a wafer or ring is placed over the stoma in a precisely centered position. Generally, one must remain in a standing position and using a mirror to achieve the centered position. The ostomy appliance is then attached to the ring and tightly secured to the skin.

Several patents and publications describe devices designed to assist ostomates in the replacement of an ostomy device, including the following patents incorporated herein by reference.

U.S. Pat. No. 6,409,709 describes an ostomy-changing facilitating device for absorbing fluids from the stoma during the change of the more permanent ostomy appliance. The ostomy-changing facilitating device includes a tubular member with absorbent material filling the bore of the tubular member.

U.S. Pat. No. 8,343,119 describes a cap device for home use to temporarily cover the stoma resulting from a urostomy, colostomy or ileostomy procedure. It provides a means of preventing leakage during routine cleaning around the stoma during the ostomy pouch replacement process.

U.S. Pat. No. 4,187,850 describes a medical-surgical method and apparatus for facilitating the replacement of ostomy appliances. A hollow cylinder, filled with sterile absorbent material is used to center the sealing ring prior to the replacement of the ostomy appliance.

U.S. Pat. No. 4,344,433 describes an appliance for facilitating replacement of a waste bag by ostomy patient comprising a base, an upright post removeably seated in said base, and a slideable collar supported on an abuttment on said post. One end of the post includes an opening which covers the stoma and collects any seepage during the replacement procedure. This particular device requires that the face plate and adhesive sealing ring be preassembled on the post and collar, after which the post is removed from the base and positioned over the stoma.

The aforementioned prior art do not include all the features and advantages of the present invention, more specifically, the present device provides an absorbent waste receptacle with a dual absorbency chamber designed to effectively collect, contain and dispose of both urine and excrement; whereas the prior art typically provides only a hollow chamber, or a chamber entirely packed with absorbent material. The device of the present invention does not require preassembly of an ostomy appliance (such as pouch and wafer) or preassembly of the device itself, therefore allowing an ostomate to take ample time to prepare and perform the pouch replacement process. Furthermore, the device of the present invention provides an absorbent waster receptacle that is customizable to a particular ostomate's stoma as well as being disposable for a sanitary and discreet disposal of waste.

BRIEF SUMMARY OF THE INVENTION

The present invention relates to an ostomy pouch replacement device that allows ostomates with a surgically created stoma to collect, contain and dispose of waste matter during frequent hygienic maintenance. In a preferred embodiment, the device consists of multiple pieces and sections, such as an optional alignment sleeve, a disposable waste receptacle, a cap or plug, and a collar stand.

One aspect of the present invention is to provide a device that is customizable to each ostomate's unique stoma diameter and provides a disposable waste receptacle for a sanitary, discreet and odorless disposal of waste. The present device can be used by a broad range of ostomates due to the dual absorbency chamber of the waste receptacle. The interior walls of the receptacle are preferably lined with absorbent material using multiple levels of absorbency to allow for the collection, containment and disposal of both urine and excrement for use in colostomies, ileostomies, and urostomies. Optionally, the absorbent section may include a superabsorbent polymer powder that becomes a gel in the presence of liquid.

Another aspect of the present invention is to provide a device that can be used during pouch replacement to provide an ostomate ample time to clean and prep the skin area surrounding the stoma, prior to attaching a clean adhesive barrier member and pouch.

DESCRIPTION OF THE DRAWINGS

These and other features, aspects, and advantages of the present invention will become better understood with regard to the following description, appended claims, and accompanying drawings where:

FIG. 1 illustrates an embodiment of the present invention whereby the apparatus is disassembled so that each component may be viewed separately;

FIG. 2 illustrates an exploded view of one embodiment of an ostomy pouch replacement device;

FIG. 3 illustrates an earlier step in the pouch replacement process whereby the device is aligned and positioned over the stoma, and the collar stand is positioned to slide over the device;

FIG. 4 illustrates a step in the pouch replacement process whereby the collar stand of the device would be pressed firmly against the stoma, thereby sealing an adhesive skin barrier to skin;

FIG. 5 illustrates a step is the pouch replacement process whereby the collar stand has been removed from the device and is positioned for use as a stand;

FIG. 6 illustrates a step in the replacement process whereby the device has been removed from the stoma and is being capped off to retain any waste contents within the waste receptacle;

FIG. 7 illustrates a step in the pouch replacement process whereby the device is capped off and ready for disposal of the waste receptacle; and FIG. 8 illustrates a step in the pouch replace replacement process whereby the used device is placed upright in the collar stand to hold the device in place and prevent spillage;

FIG. 9 illustrates one embodiment of an ostomy pouch replacement device in accordance with one aspect of the present invention, including a waste receptacle, absorbent member, and a plug; and FIG. 10 is an exploded view of the ostomy pouch replacement device shown in FIG. 9.

DETAILED DESCRIPTION OF THE INVENTION

FIG. 1 illustrates an embodiment of the present invention in a disassembled form. The device preferably consists of a disposable waste receptacle 13 for positioning the device over the stoma and for capturing any waste that may be discharged, a cap or plug 19 for sealing the device after use, and a collar stand 25 for sealing an adhesive wafer to the skin and for holding the assembled device in an upright position. The device may also consist of a reusable alignment sleeve to aid in positioning the waste receptacle 13 over the stoma. In a preferred embodiment, an absorbent member 16 comprises a first hollow portion 18 at a proximate end thereof, and a second hollow portion 17 at a distal end thereof. Both portions 17 and 18 of the absorbent member 16 are made from absorbent materials, and preferably, absorbent portion 17 includes a higher level of absorbency than absorbent portion 18. It should be understood that absorbent portion 17 may be hollow, or may not, as desired.

The waste receptacle 13 is preferably a hollow cylindrical-shaped tube, having a closed end and an open end. The open end of the tube is for positioning over a stoma (referred to herein as the "proximal end" or "stoma end"), and the opposite end (or "distal end") is preferably closed, similarly to a standard test tube. The waste receptacle 13 may be integrally formed, again, similarly to a test tube, or may include a plug or other means for sealing the distal end thereof. The diameter and dimensions of the tube 13 may be customizable depending on the shape and diameter of the stoma over which the tube is designed to fit; however, preferred dimensions are approximately 5-7 inches in length with an inner diameter sufficient to entirely surround the stoma. In a preferred embodiment, the stoma end 14 may be rounded off or include a smooth ring 15 that fits flush over the end of the receptacle 13. This ring 15 provides a more comfortable fit against an ostomate's skin, as well as forming a small inner lip at the end of the sleeve 13 for fitting flush against the absorbent member 16 once e member 16 is fully pressed against the stoma. The waste receptacle 13 may be constructed of materials such as cardboard, paper, plastic, polystyrene foam, or any other suitable disposable material. The waste receptacle 13 may also be designed from biodegradable materials such as bioplastic with an organic cotton inner lining and absorbent section.

In one embodiment, the absorbent member 16 (also referred to herein as "absorbent tube") is disposable and may be a cylindrical-shaped tube, preferably open on both ends, although it is contemplated that the distal end may be closed. The absorbent member is positioned within the waste receptacle 13 (as shown in FIG. 2) and the open end of the receptacle is positioned against the stoma for receiving waste that may be involuntarily discharged from the stoma during pouch placement. The waste material is received by the absorbent member 16, and preferably includes an absorbent and/or wicking material lining the inner surface. The dimensions of the absorbent member 16 may vary and are dependent upon the dimensions of the waste receptacle 13 and the size of the stoma. Specifically, the outer diameter of the absorbent member 16 is preferably less than the inner diameter of the waste receptacle 13, such that the absorbent member 16 may be inserted into the receptacle during production assembly, and fit snugly enough so that all waste material is directed inside the absorbent tube 16 without seepage between the tube 16 and the receptacle 13. The length of the absorbent member 16 is preferably less than the length of the receptacle 13, so that the absorbent tube 16 may be fully inserted into the receptacle 13. The length of the device may vary as desired; however, it is to be noted that when determining the appropriate length for both the waste receptacle 13 and the absorbent member 16, a greater length will provide a larger capacity for waste containment.

Examples of absorbent material include but are not limited to cotton, rayon, polyester, polyethylene, polypropylene, sodium polyacrylate, other suitable fibers, pellets, beads, and combinations thereof. The thickness of both the absorbent portions (linings or liners) 17 and 18 may vary as desired, provided the waste is absorbed as necessary. It is contemplated that the absorbent tube member 16 may be offered in a variety of absorbencies so that an ostomate may choose which is best for his or her particular needs. For example, an ostomate with a urostomy may need a tube with maximum absorbency for collecting more urine; whereas an ostomate with a colostomy may need less absorbency, for collecting more excrement.

Additionally, in another embodiment, the absorbent portion 17 may include a super absorbent polymer gel material, in order to increase the amount of absorbency of the absorbent member 16. The absorbent polymer gel is preferably a water-swollen high molecular polymer containing strong hydrophilic polymer groups, such as carboxyl or hydroxyl groups, with a certain degree of cross linking. One such absorbent polymer gel is sodium polyacrylate. The addition of the absorbent polymer gel to the absorbent portion 17 serves to increase the speed of absorption, helps to disperse the absorbed excrement evenly throughout the absorbent member 16, and provides more comfort and better drying capabilities. The absorbent polymer gel is initially in powder form, which is dispersed throughout and/or impregnated into the absorbent portion 17. When the absorbent portion 17 having the powdered super absorbent polymer comes into contact with liquid, the powder turns to a gel, and is capable of absorbing hundreds of times its own weight in water.

It should be understood that the two portions 17 and 18 of absorbent member 16 may made either from the same material or different materials, and the absorbent polymer gel may be used in either or both sections. In a preferred embodiment, the absorbent polymer gel is only used in the absorbent portion 17. This arrangement allows the absorbent polymer gel to "pull" liquid through the receptacle 13, where it is captured at the distal end of the receptacle 13 with respect to the stoma, and thus assists with the wicking process.

An optional alignment sleeve may also be provided for aiding in the positioning of the device over a stoma. The sleeve is preferably a hollow cylindrical-shaped tube, open on both ends, and adapted to receive a waste receptacle 13. The dimensions of the alignment sleeve may vary and are dependent upon the dimensions of the waste receptacle 13 and the size of the stoma. The diameter of the optional alignment sleeve is preferably greater than the outer diameter of the waste receptacle 13, such that the receptacle 13 may easily, yet snugly, slide inside the sleeve in telescopic fashion. The alignment sleeve may be constructed of materials such as plastic, polyurethane, polycarbonate, silicone rubber, or any other suitable material.

A plug 19 is preferably included to seal the proximal, or stoma, end 14 of the device after use. In one embodiment, the plug 19 is dimensioned to fit snugly and securely within the waste receptacle 13. The plug 19 preferably includes a first portion 20 that fits within the waste receptacle 13, fully sealing the receptacle 13 so that all waste is contained. A second portion 21 of the plug 19 preferably has a larger diameter than the first portion 20, for capping off or fully sealing the proximal end 14 of the waste receptacle 13. The length of the first portion 20 of the plug 19 should be such that the plug 19 fits deeply enough into the waste receptacle 13 to prevent seepage out of the tube, but not so deep that the plug is displacing any waste that may be present in the tube. The plug 19 is preferably constructed of a material such as plastic, polyurethane, polycarbonate, or any other suitable disposable material.

A collar stand 25 may be provided to aid the application of a skin barrier member such as an adhesive wafer, ring, or face, plate, during the pouch replacement process, as shown in FIG. 5. Furthermore, the collar 5 may act as a stand in which the assembled device 12 can be placed and held in an upright position, as shown in FIGS. 8 and 9. In one embodiment, the collar stand 25 consists of an open-ended cylindrical section 26 with a flange 27 on one end for providing support and stability in an upright position. The cylindrical section 26 has an inner diameter large enough to freely and easily slide the collar 25 back and forth along the full length of the waste receptacle 13, and a thickness sufficient to distribute equal and adequate force when pressing an adhesive wafer or face plate against the skin. The collar stand 25 may be constructed of any suitable material such as plastic, polyurethane, polycarbonate, silicone rubber, or stainless steel.

The ostomy pouch replacement device of the present invention may have many uses, an exemplary use being described herein The device of the present invention will be provided to an ostomate (patient) with the absorbent member 16 already inserted telescopically into the distal end of the waste receptacle 13, allowing for immediate use without much preassembly. An initial step in replacing an ostomy pouch involves removing a filled or used ostomy pouch from the adhesive barrier member (such as a wafer, sealing ring or face plate), followed by removal of the adhesive barrier member from the skin. At this point in the process, a preferred step is to center the proximal end of the waste receptacle 13 (preceded by the optional alignment sleeve, if so desired) directly over the stoma. Once the waste receptacle 13 is in place, the user can take as much time as necessary to clean and prep the skin around the stoma for application of a new skin barrier member and clean pouch. Any waste matter may involuntarily discharge at this time is captured and contained within the waste receptacle 13. Once the skin is prepped and a new adhesive barrier member is ready to be applied, the barrier member is cut to match a diameter that best fits around the stoma and is placed over the distal end of the device followed by the collar stand 25. The collar assists in sliding the wafer toward the stoma, as shown by FIG. 4, thus providing even pressure to press the wafer against the skin, ensuring tight adhesion and a good seal on the skin. Once the adhesive barrier member is applied, the collar 25 is removed and placed in an upright position, as illustrated in FIG. 5. The used device is removed or pulled away from the stoma, as shown in FIGS. 6 and 7. The waste receptacle 13 is either sealed at the proximal or stoma end 14 with the plug 19 and is placed in the stand as in FIG. 8, or alternatively placed in an upright position in e collar stand 25, as in FIG. 7, and then sealed with plug 19 to avoid any spillage of waste while allowing for free hands to attach a new pouch to the wafer or face plate.

At this point in the process both ends of the waste receptacle 13 are sealed, effective securing and containing any and all waste inside the device. Once pouch replacement is complete, the disposable waste receptacle 13 is removed from the reusable collar stand 25 and safely discarded.

Although the ostomy pouch replacement device of the present invention has been described in detail with reference to particular embodiments and dimensions, the embodiments are for illustrative purposes only and do not limit the invention. It is to be appreciated that those skilled in the art can change or modify the embodiments without departing from the scope and spirit of the invention. It is to be understood that the inventive concept is not to be considered limited to the constructions and dimensions disclosed herein.

The terms used in the present application are merely used to describe particular embodiments, and are not intended to limit the present invention. An expression used in the singular encompasses the expression of the plural, unless it has a clearly different meaning in the context present application, it is to be understood that the terms such as "including" or "having," etc., are intended to indicate the existence of the features, numbers, steps, actions, components, parts, or combinations thereof disclosed in the specification, and are not intended to preclude the possibility that one or more other features, numbers, steps, actions, components, parts, or combinations thereof may exist or may be added.

What is claimed is:

1. An ostomy pouch replacement device comprising:
   a receptacle formed as a cylindrical shaped tube and having a closed distal end and an open proximal end, said open proximal end configured and dimensioned for placement over a stoma; said receptacle containing an inner absorbent member positioned within said receptacle adjacent to said open proximal end,
   said inner absorbent member configured for receiving stoma effluent from said stoma, said inner absorbent member formed in a tubular shape and including an absorbent material dispersed therein; and
   a plug adapted and dimensioned for sealing said open proximal end of said receptacle to contain said stoma effluent and said inner absorbent member therein after use; said plug including a first portion for water-tight insertion into said open proximal end of said receptacle, and said plug further including a second portion having a larger diameter than said first portion and configured for capping off said open proximal end of said receptacle when said first portion is inserted into said open proximal end, wherein a length of said first portion is sufficient to prevent seepage of said stoma effluent from said open proximal end.

2. The ostomy pouch replacement device of claim 1,
   further including a collar stand separate from said plug and adapted for movement along an outer periphery of said receptacle between said closed distal end and said open proximal end,
   said collar stand configured by said movement to distribute pressure beyond said closed distal end or beyond said open proximal end adjacent said stoma to adhere a skin barrier member to skin surrounding said stoma, and
   said collar also comprising a flange at one end that is configured for supporting said receptacle in an upright manner.

3. The ostomy pouch replacement device of claim 1, whereby said inner absorbent member includes a first hollow portion at said proximal end of said receptacle, and a second portion at a distal end thereof for the collection, containment and disposal of both urine and excrement.

4. The ostomy pouch replacement device of claim 3, whereby said first hollow portion of said absorbent member is made from a first absorbent material, and
   a second section of said inner absorbent member includes a second absorbent material, wherein said second absorbent material includes a higher level of absorbency than said first hollow portion.

5. The ostomy pouch replacement device of claim 4, whereby said second absorbent material is selected from the group consisting of cotton, rayon, polyester, polyethylene, polypropylene, sodium polyacrylate, fibers, pellets, beads, and combinations thereof.

6. The ostomy pouch replacement device of claim 1, whereby said receptacle and said inner absorbent member are disposable.

7. The ostomy pouch replacement device of claim 1, wherein said absorbent polymer is sodium polyacrylate.

8. An ostomy pouch replacement device comprising:
   a receptacle formed as a cylindrical shaped tube and having a closed end and an open end, said open end configured and dimensioned for placement over a stoma;
   an inner absorbent member positioned within said receptacle adjacent to said open end, said inner absorbent member: of a hollow, tubular shape; adapted for receiving stoma effluent; and dimensioned to be inserted into said receptacle adjacent said open end, said inner absorbent member being infused with an absorbent polymer; and
   a plug adapted and dimensioned for sealing said open end of said receptacle to contain said stoma effluent and said inner absorbent member within said receptacle after use; said plug including: a first portion for water-tight insertion into said open proximal end of said receptacle; and a second portion having a larger diameter than said first portion and configured for capping off said open proximal end of said receptacle when said first portion is inserted into said open proximal end, wherein a length of said first portion is sufficient to prevent seepage of said stoma effluent from said open proximal end.

9. The ostomy pouch replacement device set forth in claim 8, further including a collar stand adapted for movement along an outer periphery of said receptacle between said closed end and said open end, said collar stand adapted to distribute pressure by said movement beyond said closed end or beyond said open end adjacent said stoma to adhere a skin barrier member to skin surrounding a stoma, and also including a flange at one end that is configured to support said receptacle in an upright manner.

10. A method for changing a used ostomy appliance, comprising the steps of:
   providing an ostomy pouch replacement device comprising:
      a receptacle formed as a cylindrical shaped tube and having a closed first end and an open second end, said open second end dimensioned and configured for placement over a stoma;
      an inner member including an absorbent material inserted into said receptacle adjacent said open second end and configured for collecting effluent discharged from the stoma;
      a plug including: a first portion configured for water-tight insertion into said open second end of said receptacle, and a second portion having a larger diameter than said first portion; and
      a collar stand having a flange on one end and configured to slide from said closed first end of said receptacle to said open second end thereof;
   removing said used ostomy appliance from the skin surrounding the stoma;
   centering said receptacle over the stoma such that the stoma is fully surrounded by said open second end and said absorbent material of said inner member collects said effluent discharged from the stoma within said receptacle;
   cleaning and drying the skin surrounding the stoma outside of said open second end of said receptacle;
   sliding a skin barrier member over said outer periphery of said receptacle from said first closed end to said second open end;
   sliding said collar stand: over said first closed end, along said outer periphery, and to said open second end of said receptacle, such that said skin barrier member is located between the skin surrounding the stoma and said flange of said collar stand;
   pressing said skin barrier member to the skin surrounding the stoma using said collar stand flange until said skin barrier member is securely adhered to the skin surrounding the stoma;
   removing said collar stand from said receptacle;

withdrawing said receptacle from the stoma while said receptacle contains said effluent;

capping off said open second end of said receptacle by inserting said first portion of said plug into said open second end such that said second portion caps off said open second end, wherein a length of said first portion is sufficient to prevent seepage of said stoma effluent from said open second end, such that said effluent and said absorbent material are sealed within said receptacle to form a sealed receptacle;

placing said sealed receptacle in an upright position in said collar stand such that said collar stand flange supports said sealed receptacle in an upright position; and attaching a clean ostomy pouch to said skin barrier member.

11. The method of claim 10, further including the steps of: discarding said sealed receptacle after use.

12. The method of claim 10, wherein said absorbent polymer is sodium polyacrylate.

13. A method for changing a used ostomy appliance, comprising the steps of:

providing an ostomy pouch replacement device comprising:

a receptacle formed as a cylindrical shaped tube and having an open end and a closed end, said open end configured and dimensioned for placement over a stoma;

an inner absorbent member inserted into and adjacent to said open end of said receptacle, said inner absorbent member configured for collecting and absorbing effluent discharged from the stoma, and a plug including: a first portion configured for watertight insertion into said open end of said receptacle; and a second portion having a larger diameter than said first portion;

removing said used ostomy appliance from the skin around the stoma;

centering said receptacle over the stoma such that the stoma is fully surrounded by said open first end and said inner absorbent member collects said effluent discharged from the stoma;

cleaning and drying the skin surrounding the stoma outside of said open end of said receptacle;

withdrawing said receptacle from the stoma;

capping off said receptacle by inserting said first portion of said plug into said open end such that said second portion caps off said open end, wherein a length of said first portion is sufficient to prevent seepage of said stoma effluent from said open end to seal said effluent and said inner absorbent member within said receptacle to form a sealed receptacle; and attaching a clean ostomy pouch to the skin surrounding the stoma.

* * * * *